United States Patent
Wascheck et al.

(10) Patent No.: US 7,025,803 B2
(45) Date of Patent: Apr. 11, 2006

(54) METHANE RECOVERY PROCESS

(75) Inventors: Kenneth J. Wascheck, Wilmington, DE (US); Charles L. Anderson, Wilmington, DE (US)

(73) Assignee: L'Air Liquide Societe Anonyme A Directoire et Counsel de Surveillance Pour L'Etude et L'Exploration des Procedes Georges Claude, Paris (FR)

( * ) Notice: Subject to any disclaimer, the term of this patent is extended or adjusted under 35 U.S.C. 154(b) by 224 days.

(21) Appl. No.: 10/712,620

(22) Filed: Nov. 13, 2003

(65) Prior Publication Data

US 2004/0103782 A1 Jun. 3, 2004

Related U.S. Application Data

(60) Provisional application No. 60/437,268, filed on Dec. 31, 2002, provisional application No. 60/430,270, filed on Dec. 2, 2002.

(51) Int. Cl.
*B01D 53/047* (2006.01)
*B01D 53/22* (2006.01)
*B01D 53/26* (2006.01)

(52) U.S. Cl. ............ 95/50; 95/51; 95/96; 95/98; 95/117; 95/143; 95/148; 96/4; 96/121; 96/130; 96/143

(58) Field of Classification Search ............ 95/47, 95/49–52, 96–106, 143–148, 116–121; 96/4, 96/8–10, 12, 121, 122, 130, 134, 135, 142–144
See application file for complete search history.

(56) References Cited

U.S. PATENT DOCUMENTS

| | | | | |
|---|---|---|---|---|
| 4,171,017 A | * | 10/1979 | Klass | 166/266 |
| 4,229,188 A | * | 10/1980 | Intille | 95/55 |
| 4,238,204 A | * | 12/1980 | Perry | 95/55 |
| 4,518,399 A | * | 5/1985 | Croskell et al. | 95/51 |
| 4,645,516 A | | 2/1987 | Doshi | 55/16 |
| 4,681,612 A | | 7/1987 | O'Brien et al. | 62/23 |
| 4,784,672 A | | 11/1988 | Sircar | |
| 4,934,148 A | * | 6/1990 | Prasad et al. | 62/655 |
| 4,994,094 A | * | 2/1991 | Behling et al. | 95/39 |
| 5,004,482 A | * | 4/1991 | Haas et al. | 95/52 |
| 5,015,270 A | * | 5/1991 | Ekiner et al. | 95/54 |
| 5,082,471 A | * | 1/1992 | Athayde et al. | 95/51 |
| 5,085,676 A | * | 2/1992 | Ekiner et al. | 96/13 |

(Continued)

FOREIGN PATENT DOCUMENTS

| | | |
|---|---|---|
| EP | 0 390 392 A2 | 10/1990 |
| EP | 0 312 743 B1 | 1/1993 |
| FR | 2 836 058 A | 8/2003 |

OTHER PUBLICATIONS

International Search Report for PCT/IB 03/05221.

*Primary Examiner*—Robert H. Spitzer
(74) *Attorney, Agent, or Firm*—Jeffrey C. Lew

(57) ABSTRACT

A system and a process for recovering high concentrations of methane from crude natural gas and solid waste landfill exhaust gas uses a sequential combination of a pressure swing adsorber unit operation to remove volatile organic compounds from the crude feed gas mixture followed by a membrane separation unit operation. The membrane separation uses a membrane which is selectively gas permeable to reject transmission of methane and thus to produce a permeate depleted in methane relative to the feed mixture. The permeate is also free of volatile organic compounds and is recycled to the pressure swing adsorber unit operation to regenerate saturated adsorbers.

16 Claims, 2 Drawing Sheets

U.S. PATENT DOCUMENTS

| | | | |
|---|---|---|---|
| 5,116,396 A | * 5/1992 | Prasad et al. | 62/655 |
| 5,207,806 A | * 5/1993 | Lagree et al. | 95/8 |
| 5,240,472 A | * 8/1993 | Sircar | 95/52 |
| 5,332,424 A | * 7/1994 | Rao et al. | 95/47 |
| 5,354,547 A | * 10/1994 | Rao et al. | 423/650 |
| 5,411,721 A | * 5/1995 | Doshi et al. | 423/220 |
| 5,435,836 A | * 7/1995 | Anand et al. | 95/45 |
| 5,681,360 A | 10/1997 | Siwajek et al. | 48/127.3 |
| 5,727,903 A | 3/1998 | Borray et al. | |
| 5,842,357 A | 12/1998 | Siwajek et al. | 62/625 |
| 5,968,235 A | * 10/1999 | Grime et al. | 95/123 |
| 6,221,131 B1 | * 4/2001 | Behling et al. | 95/50 |
| 2003/0084787 A1 | * 5/2003 | Hattori et al. | 95/49 |
| 2004/0099138 A1 | * 5/2004 | Karode et al. | 95/214 |
| 2004/0103782 A1 | * 6/2004 | Wascheck et al. | 95/50 |

* cited by examiner

METHANE RECOVERY PROCESS

This application claims benefit of priority of U.S. provisional patent application Ser. No. 60/437,268 filed Dec. 31, 2002 and U.S. provisional patent application Ser. No. 60/430,270 filed Dec. 2, 2002.

FIELD OF THE INVENTION

This invention relates to process for recovering methane from landfill gas. More specifically it pertains to a process that includes removing volatile organic compounds from raw landfill gas with a pressure swing absorption unit, using a selectively gas permeable membrane to separate carbon dioxide and methane from the landfill gas and using the carbon dioxide-enriched permeate stream from the membrane separation to regenerate the pressure swing absorption unit.

BACKGROUND OF THE INVENTION

Solid waste landfills contain enormous quantities of diverse waste materials. These materials decompose with time and produce a wide variety of decomposition products. It is common for solid waste landfills in this manner to generate large volumes of exhaust gas containing among other things, methane, carbon dioxide, hydrogen sulfide, and gases of many hydrocarbon and other organic compounds. These hydrocarbon and other organic compounds are well known air pollutants and are collectively referred to herein as volatile organic compounds or "VOC".

Typical landfill exhaust gas contains high concentrations of methane and carbon dioxide, water vapor, and lesser concentrations of VOC's and other contaminants. Methane is commonly known as natural gas and is valuable commercial commodity as a combustible fuel for supplying energy and also as a raw material in many industrial significant processes. Thus it is very desirable from an economic viewpoint to capture the methane from landfill exhaust gas.

If landfill exhaust gas is not recovered, the methane escaping into ambient air presents a considerable source of air pollution. Accordingly, it is further desirable to prevent the methane from landfill exhaust gas for environmental protection purposes. Traditionally, landfill exhaust gas has been prevented from escaping to the environment by burning it in an open flame incinerator such as a flare stack. This process is inefficient. Consequently, a large fraction of the methane and other obnoxious contaminants in the exhaust gas survive to pollute the ambient air. Also, flare stack operation is a waste of the useful energy held by the methane in the exhaust gas.

Other conventional methods of recovering methane from landfill exhaust gas and other sources of crude natural gas have developed. These include gas separation processes in which the useful methane is separated from the other components of the source gas. Favored conventional gas separation processes typically utilize adsorption-regeneration technology in which the crude gas is passed through an adsorbent material that rejects selected components of the crude and rejects others. For example, pressure swing adsorption ("PSA") or Thermal Swing Adsorption ("TSA") technologies involve selectively adsorbing contaminants of crude gas onto adsorbent particles and allowing the so-called sweetened gas to pass through the PSA/TSA units.

Unfortunately, the adsorbent particles ultimately become saturated with the contaminants and lose ability to adsorb beyond a maximum amount. Before more contaminants can be removed from the crude, the adsorbent particles must be regenerated. This normally involves exposing the saturated particles to high temperatures, and fluids that have low concentrations of the contaminants to promote desorption of the contaminants from the particles. For example, TSA requires a supply of high pressure steam and PSA requires a supply of clean, usually low pressure gas. Additionally, adsorption-regeneration technology normally also requires support facilities for removal of water vapor, and pre-conditioning the crude gas, e.g., by compressing it to high pressure. Thus it is very costly in financial and energy consumption aspects to operate conventional adsorption-regeneration technologies for recovering useful methane from crude natural gas and landfill exhaust gas.

SUMMARY OF THE INVENTION

This invention is directed to providing for the safe, economical, environmentally protective recovery of methane on a commercially viable scale from solid waste landfill exhaust gas, crude natural gas and other mixtures of methane with noxious contaminants.

Accordingly, there is now provided, a system for recovering methane from a feed mixture comprising methane, carbon dioxide and volatile organic compounds, the system comprising, a pressure swing adsorption unit having a bed of adsorbent particles and operative to adsorb volatile organic compounds from the feed mixture onto the particles so as to produce an intermediate mixture of gases having composition reduced in volatile organic compounds relative to the feed mixture, and operative to desorb the volatile organic compounds from particles into a regenerating gas, a primary gas separation module comprising a membrane which is selectively gas permeable to carbon dioxide relative to methane, a feed-retentate chamber within the module on a first side of the membrane, and a permeate chamber within the module on a second side of the membrane, in which the feed-retentate chamber is in fluid communication with the bed of the pressure swing adsorption unit in a manner adapted to permit transfer of the intermediate mixture into the feed-retentate chamber in contact with the first side of the membrane, a retentate discharge line in fluid communication with the feed-retentate chamber adapted to withdraw from the module a retentate gas having composition enriched in methane relative to the intermediate mixture, a permeate discharge line in fluid communication between the permeate chamber of the module and the bed of the pressure swing adsorption unit and which is operative to transfer a permeate gas having composition depleted in methane relative to the intermediate mixture and which permeate gas is adapted to receive desorbed volatile organic compounds from the particles of the bed to form a spent regenerating gas, and a thermal oxidizing unit in fluid communication with the pressure swing adsorption unit which is operative to destroy the volatile organic compounds in the spent regenerating gas and to produce a vent gas having composition substantially free of volatile organic compounds.

There is further provided a process for separating methane from a feed mixture comprising methane, carbon dioxide and volatile organic compounds that utilizes a pressure swing adsorption unit operation to remove the volatile organic compounds from the feed mixture to form an intermediate mixture and a selectively gas permeable membrane to separate methane from the intermediate mixture and thereby produce a permeate gas having composition depleted in methane relative to the intermediate mixture in which the improvement comprises regenerating the pressure swing adsorption units by conducting the permeate gas through the pressure swing adsorption units which become saturated with the volatile organic compounds.

Additionally, this invention provides a process for separating methane from a feed mixture comprising methane, carbon dioxide and volatile organic compounds comprising the steps of:

(A) providing a plurality of pressure swing adsorption units each having a bed of adsorbent particles operative to reversibly adsorb the volatile organic compounds from the feed mixture onto the particles, (B) charging the feed mixture into an active pressure swing adsorption unit and contacting the feed mixture with the adsorbent particles under operating conditions including pressure and temperature to cause the volatile organic compounds to adsorb onto the particles, (C) withdrawing from the active pressure swing adsorption unit an intermediate mixture having composition reduced in volatile organic compounds relative to the feed mixture, (D) when the bed of adsorbent particles in the active pressure swing adsorbent unit has adsorbed a preselected amount of volatile organic compounds, stopping steps (B) and (C) thereby deactivating the pressure swing adsorbent unit, (E) providing a primary gas separation module comprising a membrane which is selectively gas permeable to carbon dioxide relative to methane, a feed-retentate chamber within the module on a first side of the membrane, and a permeate chamber within the module on a second side of the membrane, (F) introducing the intermediate mixture into the feed-retentate chamber of the primary module in contact with the membrane and causing the intermediate mixture to selectively permeate through the membrane into the permeate chamber, (G) removing from the feed-retentate chamber of the primary module a retentate gas having composition enriched in methane relative to the intermediate mixture, (H) removing from the permeate chamber of the primary module a permeate gas having composition reduced in concentration of methane relative to the intermediate mixture, (I) conducting the permeate gas through the bed of adsorbent particles in at least one of the deactivated pressure swing adsorption units under operating conditions including pressure, temperature and duration effective to desorb volatile organic compounds from the bed to form a spent regenerating gas within the deactivated pressure swing adsorption unit, (J) withdrawing the spent regenerating gas from the deactivated pressure swing adsorption unit, (K) when the bed of particles in the deactivated pressure swing adsorption unit attains a loading inventory below a pre-selected value of parts by weight volatile organic compounds per 100 parts by weight adsorbent particles, stopping steps (I) and (J) thereby activating the deactivated pressure swing adsorption unit.

DETAILED DESCRIPTION OF THE INVENTION

Figure 1:
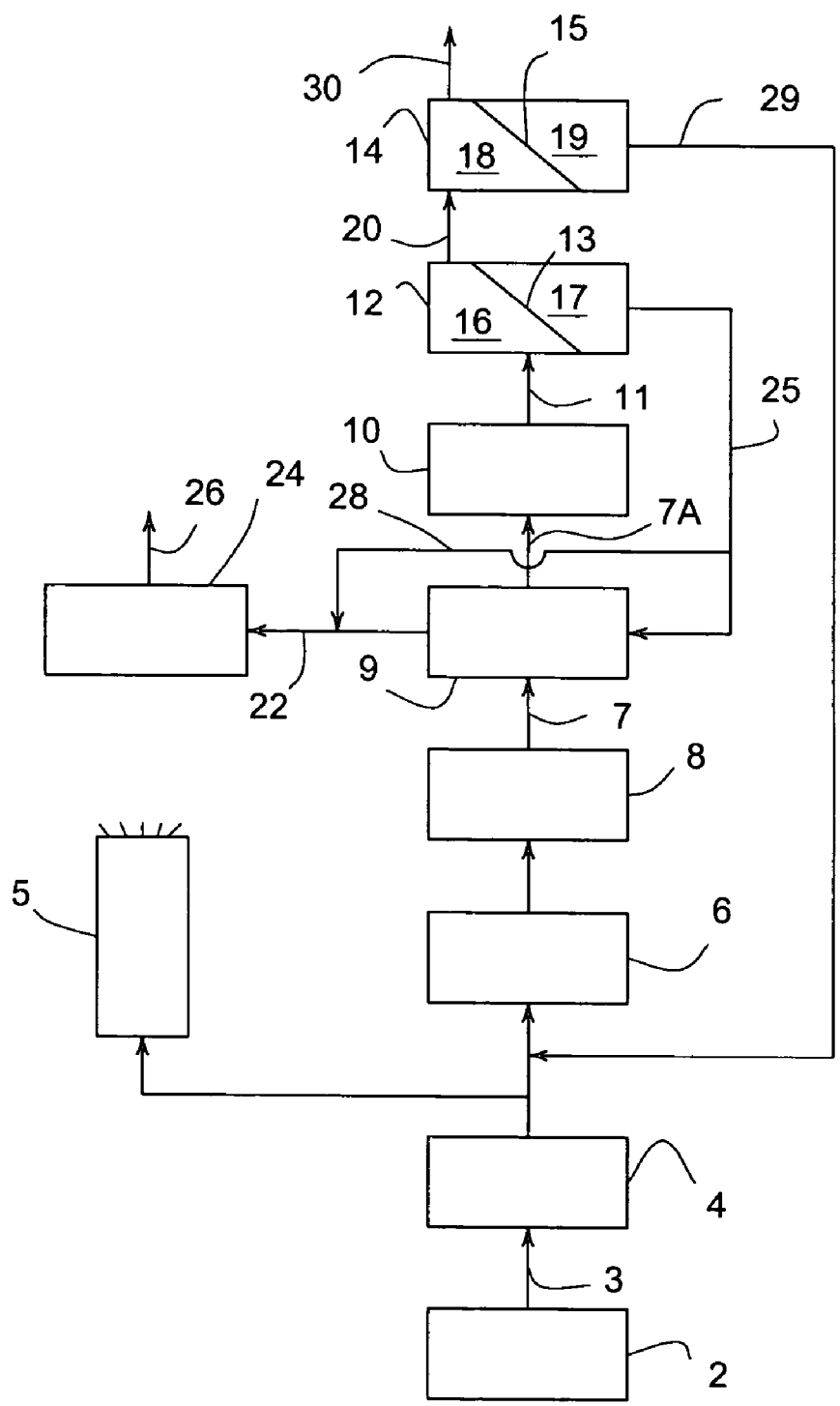
FIG. 1 is a schematic flow diagram of an embodiment of the present invention.

The present invention provides a system and process for recovering a high concentration of methane gas from a crude feedstock such as crude natural gas or the exhaust gas from a solid waste landfill. The recovered methane produced by the system and process is substantially free of impurities and thus useful as a feedstock in industrial processes and products or as a combustible fuel to supply energy for industrial processes. As used throughout this disclosure the term "substantially" means that the referenced condition exists largely but not necessarily completely. For example, in reciting that the recovered methane is "substantially free of impurities" means that the recovered methane is largely free of impurities but can have small concentrations such as trace amounts, parts per million or up to a few percent of such impurities which do not adversely affect the quality of the product or the operation of the process.

Generally this invention uses a combination of pressure swing adsorption and selectively permeable gas separation membrane technologies. It can be understood with reference to FIG. 1 which illustrates a schematic flow diagram of a preferred embodiment thereof.

Exhaust gas 3 from a solid waste landfill 2 is conveyed into the suction of a compressor 6 with a blower 4. The blower has the optional ability to force the exhaust gas to a flare stack 5 where combustible components of the gas can be incinerated conventionally when the methane recovery system is temporarily non-functional, for example, to effect repairs. The compressor pressurizes the raw exhaust gas to a high pressure suitable for removing the VOC's in the pressure swing adsorption unit ("PSA") 9, downstream.

Immediately downstream of compressor 6 is a set of coalescing filters 8 which strip liquid contaminants from the gas. The coalescing filters remove such substances as compressor lubrication oil, condensed water vapor and some higher boiling VOC's. Multiple stages of coalescing filters can be used although the flow diagram shows only one unit as being present. The liquid residue from the coalescing filters is collected and usually disposed of by appropriate waste liquid treatment facilities, not shown.

The substantially liquid-free and pressurized feed mixture 7 of methane, carbon dioxide, VOC's and other possible contaminants, such as hydrogen sulfide and siloxanes is charged into the PSA unit 9. Again, while only one PSA unit is illustrated, it is preferred that at least two PSA elements are deployed in a commercially practicable installation. The reasons for having multiple PSA elements will be explained in greater detail below. As represented in FIG. 1, the feed mixture enters the PSA unit and a major fraction of the VOC's are adsorbed by beds of particles of suitably chosen adsorbent material within the PSA elements.

The PSA units are typically of conventional construction. They generally are tanks containing beds of adsorbent particles positioned on a porous support such as a wire mesh screen or perforated plate. Gas to be treated in the PSA is conducted through the support and the interstices between the particles so at to maximize contact with the adsorbent material. Any adsorbent material that is selective to volatile organic compounds can be used. Representative adsorbent particle compositions are activated alumina, silica gel, activated carbon and mixtures thereof.

The gas mixture from the PSA unit preferably is further processed through an activated carbon bed 10 to remove most of the small residual amounts of VOC's that survived PSA treatment. Preferably, the activated carbon bed completely removes VOC's from the PSA-treated gas mixture. More preferably, the activated carbon bed combined with the PSA unit is effective to completely remove siloxanes present in the feed gas mixture provided by the waste landfill. Again, multiple activated carbon elements can be used. The intermediate mixture 11 withdrawn from the PSA units thus has a composition which is much reduced in concentration of volatile organic compounds than the feed mixture 3.

Next the intermediate mixture of gases is introduced into at least one (hereinafter the "primary") gas separation module 12. This is a device that can be generally described as having a membrane 13 within a case such that the membrane defines two compartments, namely a feed-retentate chamber 16, and a permeate chamber 17 inside the module. The membrane comprises a gas permeable substance that exhibits a selectivity for methane relative to other components of the intermediate mixture. Usually, the selectively gas permeable substance is less preferentially permeable to methane than the other components. The intermediate gas mixture should be at an elevated pressure in the feed-retentate chamber. This pressure is determined by the discharge pressure of compressor 6 and the pressure drop experienced by the gas as it flows through the coalescing filters, PSA unit and activated carbon filter. Thus there is a driving force sufficient to cause the intermediate mixture to selectively permeate the membrane 13. Consequently, a permeate gas 25 having a composition that is depleted in methane relative to the intermediate mixture composition is provided in the permeate chamber 17. Similarly, a retentate gas 20 forms in the feed-retentate chamber 16. Because the membrane tends to reject methane, the concentration of methane in the retentate gas is enriched relative to the intermediate mixture composition. Depending on the intended use of the product methane gas, the retentate gas 20 from the primary module may be of sufficient purity that it can be used directly without further purification.

Preferably, a secondary gas separation module 14 is provided to further "sweeten", i.e., purify, the methane product. This module has a selectively gas permeable membrane 15 which divides the module 14 into a secondary feed-retentate chamber 18 and a secondary permeate chamber 19. The retentate gas 20 from the primary module 12 is introduced into the secondary feed-retentate chamber 18 where it contacts the membrane 15. Methane is again rejected by the membrane so that a secondary retentate gas 30 of higher methane concentration is produced. This product is usually of adequate quality for consumption as a process feedstock or a combustible fuel. Additional separation stages may be utilized as the need arises.

In an important aspect of the present invention, the permeate gas 25 from the primary separation module is returned to the PSA unit 9 to regenerate the beds of adsorbent particles therein. This permeate gas is at a satisfactorily low pressure to facilitate the desorption of the VOC's from the particles. Consequently the energy invested in compressing the gas 3 by compressor 6 is conserved by blowing the permeate gas through the PSA unit as compared to venting the permeate and having to pressurize another regeneration gas. The permeate gas is suitably conditioned as having been filtered and dried. It is also cleaned of VOC's. Moreover, it has a low concentration of methane, and therefore, little of the useful methane in the initial feedstock is wasted by regenerating the PSA unit with the permeate gas. Thus the permeate gas 25 is ideal for regenerating the PSA unit.

When the PSA unit status is switched from active (i.e., available to, or in process of adsorbing VOC from the feed mixture, to deactivate (i.e., ready to be, or in process of being regenerated), the particles have VOC adsorbed on them. Until these adsorbed VOC's are removed, the particles are unable to adsorb more and the separation of the VOC's from the feed mixture ceases to occur. The VOC's are removed from the particles by providing a driving force to desorb the VOC'S. The regeneration step of the pressure swing adsorption process involves exposing the adsorbent particles in the bed to a low pressure atmosphere having a low concentration of VOC's. This invention provides that the regenerating atmosphere is provided by the returning permeate gas 25, as mentioned above.

During regeneration the VOC's leave the adsorbent particles and enter the regenerating gas stream 22, sometimes referred to herein as spent regeneration gas. The waste VOC's in the regeneration gas can be destroyed to avoid pollution to the environment. Destruction of the VOC's can be achieved by any of many well known methods in the art. Preferably, the spent regeneration gas 22 is processed in a high efficiency incinerator 24, sometimes referred to as a thermal oxidizing unit. Preferably the incinerator serves to decompose at least about 98% of the VOC's to benign combustion products such as water and carbon dioxide in a safe and controlled manner. The incinerated spent regeneration gas 26 can then be safely vented to atmosphere without adversely affecting the environment. Permeate gas 28 in excess of the amount needed to regenerate the PSA unit or which is produced while the PSA unit is not regenerating bypasses the PSA unit and is incinerated prior to venting to the atmosphere.

When secondary or higher order additional membrane separation stages are present, the permeate gas 29 from these stages will usually contain high (i.e., greater than about 40%) concentrations of methane and carbon dioxide and up to a few percent of other gases such as nitrogen and oxygen. This permeate gas can be recycled to the suction of compressor 6 for reprocessing to recover the methane that had permeated the membrane modules.

In a typical installation of the present invention at a solid waste landfill site, the landfill can be expected to generate about 5 million standard (i.e., at 0° C. temperature and 1 atmosphere pressure) cubic feet ("SCF") per day of exhaust gas 3. This landfill exhaust gas can have a composition about as follows: 50% methane, 44% carbon dioxide, 5% nitrogen, 1% oxygen, 50 parts per million ("ppm") hydrogen sulfide, 200 ppm VOC's and a saturated amount of water vapor. Gas mixture composition percentages herein are on a volume basis unless specified otherwise. Compressor 6 would thus be sized to compress about 7.2 million SCF per day from about atmospheric to 200 psi pressure. The approximately 290 million BTU per day of energy consumed by the compressor can be provided by the gas product 30 of the process. Substantially all of the VOC's are adsorbed by the PSA unit and the activated carbon bed. Thus the retentate gas product of the primary membrane separation stage 12 should have a composition of approximately the following concentrations: 75% methane, 20% carbon dioxide, 4% nitrogen, 1% oxygen, 50 parts per million ("ppm") hydrogen sulfide. The primary permeate gas will thus be about 2.3 million SCF per day and have a composition of approximately the following concentrations: 90% carbon dioxide, 8% methane and 2% nitrogen and oxygen combined. Fuel for the compressor consumes about 0.34 million SCF per day of retentate gas. The balance of the retentate gas at about 100 psig should provide about 2.4 million SCF per day of product having about 85% methane, less than about 5 ppm of hydrogen sulfide and less than 1% water vapor.

Figure 2:
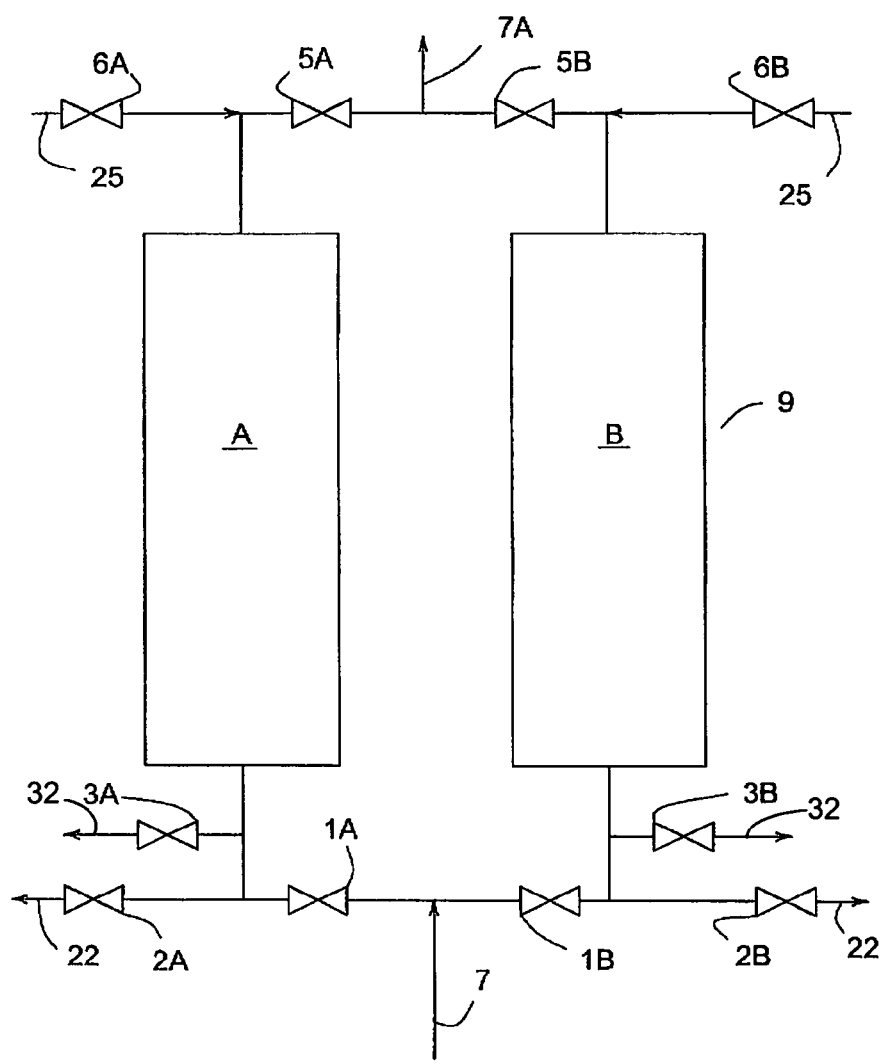
FIG. 2 is a schematic flow diagram of a pressure swing adsorber unit utilized in an embodiment of the present invention.

Operation of the process of this invention can be further understood with reference to FIG. 2 which illustrates a flow diagram for a PSA unit that includes two pressure swing adsorbers A and B. The adsorbers can from time to time be switched between active status and deactivated status as desired to maintain continuous operation. To understand the basic flow scheme, assume that adsorber A is presently active, that is, removing VOC from the feed mixture, and that adsorber B is presently deactivated, that is, regenerating the adsorbent particles. Thus the feed mixture gas 7 enters the PSA unit and intermediate mixture gas 7A exits toward the primary membrane separator. Permeate gas line 25 from the primary membrane module divides (not shown) and enters to regenerate the PSA unit through valves 6A and 6B. Similarly, the spent regeneration gas originates at lines 22 which join (not shown) prior to entering the incinerator 24, FIG. 1. Accordingly, valves 1A, 5A, 2B, and 6B, are open, and valves 2A, 6A, 1B and 5B are closed. Transfer lines 32 join (not shown) and return to the feed mixture suction of compressor 6, consequently valves 3A and 3B are closed except as will be explained.

Regeneration of a saturated adsorber, e.g., adsorber B, is carried out as follows. Directly after deactivating adsorber B by closing valves 5B and 1B (valves 6B, 3B, and 2B, being closed at this time), the high pressure in the adsorber must be relieved to provide a suitable pressure for desorbing the VOC's from the adsorbent particles. This is accomplished by opening valve 3B which permits the compressor 6 to draw VOC-containing gas from adsorber B back to the compressor for treatment by a then currently activated adsorber. When the pressure has reduced in adsorber B sufficiently to permit desorption, valve 3B is closed and valves 2B and 6B are opened. Valves 2B and 6B are throttled so that the depressurization of the adsorber occurs in a controlled manner such that the bed of particles is not disturbed by too rapid a release of high pressure gas. With valves set as described, the substantially VOC-free, permeate gas flows from line 25 through the bed, picks up the desorbed VOC's from the adsorbent particles and carries the spent regeneration gas 22 into the incinerator for controlled destruction of the VOC's. After the VOC's have been desorbed from the particles in adsorber B, valves 2B and 6B are closed. To place adsorber B in condition to remove VOC's from the feed mixture, the adsorber must be pressurized. Preferably it is pressurized by backflushing VOC-free, intermediate mixture gas 7A through valve 5B while valve 1B remains closed. Adsorber B could be pressurized with feed mixture gas 7, however this would bring VOC's into the adsorber at too low a pressure to adsorb onto the particles. The VOC's in the adsorber would then pass forward into the product when the adsorber is placed in activated status. This problem is obviated by backflushing with intermediate mixture gas. When adsorber B is pressurized, it can be activated by opening valve 1B which allows feed gas to flow through the bed of adsorbent particles and to discharge to the primary membrane module. While adsorber B is deactivated for regeneration, adsorber A is in active status and thus is removing VOC's from the feed mixture. When the bed of particles in adsorber A reach saturation with VOC's, this adsorber can be deactivated and regenerated in a manner analogous to the method just described in relation to adsorber B.

In typical operation, the feed gas 7 to an adsorber is at about 200 psig pressure and about 45° C. The feed gas is water saturated and is composed of about 44% carbon dioxide, 50% methane, 5% air (i.e., nitrogen and oxygen), about 100 ppm hydrogen sulfide and about 200 ppm VOC's. Typical VOC's in the feed mixture are ethylbenzene, toluene and xylene. The feed gas is stripped substantially completely of VOC's by passing through aluminum oxide adsorbent particles in a vertically oriented cylindrical. To regenerate the bed after the adsorbent particles become saturated with VOC's, a flow of primary membrane module permeate gas at about 5 psig and 45° C. is utilized. The permeate is about 90% carbon dioxide, about 8% methane, about 2% air, about 2 times the concentrations of water and hydrogen sulfide present in the mixture and substantially no VOC's.

The membrane used in primary, secondary and optionally higher order gas separation membranes is typically an organic polymer selected from among polymers having selectivity between methane and carbon dioxide. The polymers are usually glassy and rigid, and therefore, may be used to form a single-layer membrane of an unsupported film or fiber of the polymer. Such single-layer films are normally too thick to yield commercially acceptable transmembrane flux of the preferentially permeable component of the feed mixture. To be more economically practical, the separation membrane can comprise a very thin selective layer that forms part of a thicker structure. This structure may be, for example, an asymmetric membrane, which comprises a thin, dense skin of selectively permeable polymer and a thicker micro-porous support layer which is adjacent to and integrated with the skin. Such membranes are described, for example, in U.S. Pat. No. 5,015,270 to Ekiner.

In a preferred embodiment, the membrane can be a composite membrane, that is, a membrane having multiple layers of typically different compositions. Modern composite membranes typically comprise a porous and non-selective support layer. It primarily provides mechanical strength to the composite. A selective layer of another material that is selectively permeable, is placed coextensively on the support layer. The selective layer is primarily responsible for the separation properties. Typically, the support layer of such a composite membrane is made by solution-casting a film or spinning a hollow fiber. Then the selective layer is usually solution coated on the support in a separate step. Alternatively, hollow-fiber composite membranes can be made by co-extrusion of both the support material and the separating layer simultaneously as described in U.S. Pat. No. 5,085,676 to Ekiner.

The membranes of the invention may be housed in any convenient type of separation unit. For example, flat-sheet membranes can be stacked in plate-and-frame modules or wound in spiral-wound modules. Hollow-fiber membranes are typically potted with a thermoset resin in cylindrical housings. The final membrane separation unit can comprise one or more membrane modules. These can be housed individually in pressure vessels or multiple modules can be mounted together in a common housing of appropriate diameter and length.

Although specific forms of the invention have been selected for illustration in the drawings and the preceding description is drawn in specific terms for the purpose of describing these forms of the invention fully and amply for one of average skill in the pertinent art, it should be understood that various substitutions and modifications which bring about substantially equivalent or superior results and/or performance are deemed to be within the scope and spirit of the following claims.

The invention claimed is:

1. A process for separating methane from a feed mixture comprising methane, carbon dioxide and volatile organic compounds that utilizes a plurality of pressure swing adsorption units to remove some of the volatile organic compounds from the feed mixture to form an intermediate mixture and a selectively gas permeable membrane to separate methane from the intermediate mixture and thereby produce a permeate gas having composition depleted in methane relative to the intermediate mixture, in which the improvement comprises regenerating the pressure swing adsorption units by conducting the permeate gas through the pressure swing adsorption units which have adsorbed a preselected amount of the volatile organic compounds and processing the intermediate feed mixture through a polishing bed of activated carbon upstream of the selectively gas permeable membrane and therein further reducing the concentration of volatile organic compounds in the intermediate mixture.

2. The process of claim 1 in which the pressure swing adsorption units contain a loaded inventory of parts by weight volatile organic compounds per 100 parts by weight adsorbent particles when saturated and which process further comprises conducting the permeate gas through the pressure swing adsorption units under operating conditions including pressure, temperature and duration effective to remove at least about 90% of the loaded inventory.

3. A process for separating methane from a feed mixture comprising methane, carbon dioxide and volatile organic compounds comprising the steps of:
  (A) providing a plurality of pressure swing adsorption units each having a bed of adsorbent particles operative to reversibly adsorb the volatile organic compounds from the feed mixture onto the particles and a polishing bed of activated carbon in fluid communication downstream of the plurality of pressure swing adsorption units,
  (B) charging the feed mixture into an active pressure swing adsorption unit and contacting the feed mixture with the adsorbent particles under operating conditions including pressure and temperature to cause the volatile organic compounds to adsorb onto the particles,
  (C) withdrawing from the active pressure swing adsorption unit an intermediate mixture having composition reduced in volatile organic compounds relative to the feed mixture,
  (D) when the bed of adsorbent particles in the active pressure swing adsorbent unit has adsorbed a preselected amount of volatile organic compounds, stopping steps (B) and (C) thereby deactivating the pressure swing adsorbent unit,
  (E) providing a primary gas separation module comprising a membrane which is selectively gas permeable to carbon dioxide relative to methane, a feed-retentate chamber within the module on a first side of the membrane, and a permeate chamber within the module on a second side of the membrane,
  (F) in the polishing bed reducing the concentration of volatile organic compounds of the intermediate mixture and introducing the intermediate mixture into the feed-retentate chamber of the primary module in contact with the membrane and causing the intermediate mixture to selectively permeate through the membrane into the permeate chamber,
  (G) removing from the feed-retentate chamber of the primary module a retentate gas having composition enriched in methane relative to the intermediate mixture,
  (H) removing from the permeate chamber of the primary module a permeate gas having composition reduced in concentration of methane relative to the intermediate mixture,
  (I) conducting the permeate gas through the bed of adsorbent particles in at least one of the deactivated pressure swing adsorption units under operating conditions including pressure, temperature and duration effective to desorb volatile organic compounds from the bed to form a spent regenerating gas within the deactivated pressure swing adsorption unit,
  (J) withdrawing the spent regenerating gas from the deactivated pressure swing adsorption unit,
  (K) when the bed of particles in the deactivated pressure swing adsorption unit attains a loading inventory below a pre-selected value of parts by weight volatile organic compounds per 100 parts by weight adsorbent particles, stopping steps (I) and (J) thereby activating the deactivated pressure swing adsorption unit.

4. The process of claim 3 which further comprises diverting flows of feed mixture and permeate gas to active and deactivated pressure swing adsorption units, respectively, and repeating steps (B)–(D) and (I)–(K) as appropriate to maintain a continuous removal of retentate gas and permeate gas from the primary gas separation module.

5. The process of claim 4 which further comprises
  (i) providing a secondary gas separation module comprising a membrane which is selectively gas to carbon dioxide relative to methane, a secondary feed-retentate chamber within the module on a first side of the membrane, and a secondary permeate chamber within the module on a second side of the membrane,
  (ii) feeding the retentate gas from the primary module into the secondary feed-retentate chamber and causing the retentate gas to selectively permeate through the membrane of the secondary module into the secondary permeate chamber,
  (iii) removing from the secondary feed-retentate chamber of a second retentate gas having composition enriched in methane relative to the retentate gas of the primary module.

6. The process of claim 5 which further comprises removing from the secondary permeate chamber a secondary permeate gas having composition reduced in methane relative to the retentate gas of the primary module and recycling at least a portion of the secondary permeate gas into the feed mixture.

7. The process of claim 3 which further comprises thermally oxidizing the spent regenerating gas under conditions of pressure, temperature and duration effective to destroy substantially all of the volatile organic compounds therein.

8. The process of claim 3 in which the feed mixture comprises exhaust gas recovered from a solid waste landfill.

9. The process of claim 8 in which the feed mixture further comprises siloxanes and the combination of pressure swing adsorption unit and polishing bed of activated carbon is effective to substantially completely remove the siloxanes from the feed mixture.

10. The process of claim 3 in which the feed mixture comprises water and in which the process further includes removing water from the feed mixture in the pressure swing adsorption units.

11. A system for recovering methane from a feed mixture comprising methane, carbon dioxide and volatile organic compounds, the system comprising,
  a pressure swing adsorption unit having a bed of adsorbent particles and operative to adsorb volatile organic compounds from the feed mixture onto the particles so as to produce an intermediate mixture of gases having composition reduced in volatile organic compounds relative to the feed mixture, and operative to desorb the volatile organic compounds from particles into a regenerating gas, a primary gas separation module comprising a membrane which is selectively gas permeable to carbon dioxide relative to methane, a feed-retentate chamber within the module on a first side of the membrane, and a permeate chamber within the module on a second side of the membrane, in which the feed-retentate chamber is in fluid communication with the bed of the pressure swing adsorption unit in a manner adapted to permit transfer of the intermediate mixture into the feed-retentate chamber in contact with the first side of the membrane, a polishing bed of activated carbon in fluid communication between the pressure swing adsorption unit and the primary gas separation module, a retentate discharge line in fluid communication with the feed-retentate chamber adapted to withdraw from the module a retentate gas having composition enriched in methane relative to the intermediate mixture, a permeate discharge line in fluid communication between the permeate chamber of the module and the bed of the pressure swing adsorption unit and which is operative to transfer a permeate gas having composition depleted in methane relative to the intermediate mixture and which permeate gas is adapted to receive desorbed volatile organic compounds from the particles of the bed of the pressure swing adsorption unit to form a spent regenerating gas, and a thermal oxidizing unit in fluid communication with the pressure swing adsorption unit which is operative to destroy the volatile organic compounds in the spent regenerating gas and to produce a vent gas having composition substantially free of volatile organic compounds.

12. The system of claim 11 which further comprises a secondary gas separation module comprising a membrane which is selectively gas permeable to methane relative to carbon dioxide, a secondary feed-retentate chamber within the module on a first side of the membrane, and a secondary permeate chamber within the module on a second side of the membrane, in which the secondary feed-retentate chamber is in fluid communication with the retentate discharge line of the primary gas separation module in a manner adapted to permit transfer of the retentate gas from the primary module into the secondary feed-retentate chamber.

13. The system of claim 12 which further comprises a recycle transfer line in fluid communication with the secondary feed-retentate chamber and adapted to return a recycle stream of gas permeated through the membrane of the secondary gas separation module into the feed mixture.

14. The system of claim 11 which further comprises at least one additional pressure swing adsorption unit such that a plurality of pressure swing adsorption units connected in parallel fluid communication is present in a manner adapted to transfer the feed mixture through the bed of at least one active pressure swing adsorption unit and the polishing bed of activated carbon and into the feed-retentate chamber of the primary gas separation module, and to simultaneously transfer the permeate gas from the primary gas separation module through the bed of at least one regenerating pressure swing adsorption unit other than the active unit.

15. The system of claim 11 in which the adsorbent particles comprise adsorbent materials selected from the group consisting of activated alumina, silica gel, activated carbon and mixtures thereof.

16. The system of claim 11 in which the adsorbent particles are selected from the group consisting of activated alumina, silica gel and a mixture thereof.

* * * * *